(12) United States Patent
Belalcazar

(10) Patent No.: US 7,366,569 B2
(45) Date of Patent: *Apr. 29, 2008

(54) NON-INVASIVE METHOD AND APPARATUS FOR CARDIAC PACEMAKER PACING PARAMETER OPTIMIZATION AND MONITORING OF CARDIAC DYSFUNCTION

(75) Inventor: Hugo Andres Belalcazar, Bogota (CO)

(73) Assignee: Cardiac Pacemakers, Inc., St. Paul, MN (US)

( * ) Notice: Subject to any disclaimer, the term of this patent is extended or adjusted under 35 U.S.C. 154(b) by 395 days.

This patent is subject to a terminal disclaimer.

(21) Appl. No.: 10/941,427

(22) Filed: Sep. 15, 2004

(65) Prior Publication Data

US 2005/0043767 A1   Feb. 24, 2005

Related U.S. Application Data

(63) Continuation of application No. 09/993,351, filed on Nov. 16, 2001, now Pat. No. 6,832,113.

(51) Int. Cl.
*A61N 1/365* (2006.01)

(52) U.S. Cl. .......................................... 607/23; 607/17

(58) Field of Classification Search ...................... None
See application file for complete search history.

(56) References Cited

U.S. PATENT DOCUMENTS

| | | | | |
|---|---|---|---|---|
| 4,519,395 | A | 5/1985 | Hrushesky | 128/671 |
| 4,922,907 | A | 5/1990 | Hedin et al. | 128/419 P |
| 4,930,518 | A | 6/1990 | Hrushesky | 128/671 |
| 5,156,147 | A | 10/1992 | Warren et al. | 128/419 PG |
| 5,168,869 | A | 12/1992 | Chirife | 128/419 PG |
| 5,188,106 | A | 2/1993 | Nappholz et al. | 128/419 PG |
| 5,197,467 | A | 3/1993 | Steinhaus et al. | 128/419 PG |

(Continued)

FOREIGN PATENT DOCUMENTS

DE  19720755  11/1998

(Continued)

OTHER PUBLICATIONS

"Itimar Medical and Medtronic Announce Further Cooperation to Advance Diagnostic Innovation", *Business Wire*, p. 1254, Full text provided by Dialog,(May 9, 2000),2 pgs.

(Continued)

*Primary Examiner*—Carl Layno
(74) *Attorney, Agent, or Firm*—Schwegman, Lundberg & Woessner, P.A.

(57) ABSTRACT

A plethysmogram signal is sensed from a patient and provided to a programmer device for monitoring the condition of the patient and for optimizing pacing parameters of a cardiac device implanted in the patient. The programmer device analyzes the plethysmogram signal for cardiac performance associated with different pacing parameters. The cardiac performance is indicated by, for example, a pulse amplitude response, a degree of pulsus alternans, or irregularity in the pressure pulses detected in an atrial fibrillation patient. The pacing parameters resulting in the best cardiac performance are selected as the optimum pacing parameters. In one embodiment, the programmer device monitors a Valsalva maneuver performed by a patient. Optimum pacing parameters are derived by analysis of the plethysmogram signals obtained during performance of the Valsalva maneuver while the patient is paced using different pacing parameters.

35 Claims, 7 Drawing Sheets

U.S. PATENT DOCUMENTS

| | | | |
|---|---|---|---|
| 5,291,895 A | 3/1994 | McIntyre | 128/672 |
| 5,312,452 A | 5/1994 | Salo | 607/17 |
| 5,318,595 A | 6/1994 | Ferek-Petric et al. | 607/17 |
| 5,330,511 A | 7/1994 | Boute | 607/25 |
| 5,334,222 A | 8/1994 | Salo et al. | 607/17 |
| 5,413,592 A | 5/1995 | Schroeppel | 607/18 |
| 5,417,717 A | 5/1995 | Salo et al. | 607/18 |
| 5,454,838 A | 10/1995 | Vallana et al. | 607/19 |
| 5,466,245 A | 11/1995 | Spinelli et al. | 607/17 |
| 5,487,752 A | 1/1996 | Salo et al. | 607/17 |
| 5,514,163 A | 5/1996 | Markowitz et al. | 607/9 |
| 5,527,347 A | 6/1996 | Shelton et al. | 607/9 |
| 5,534,016 A | 7/1996 | Boute | 607/9 |
| 5,540,727 A | 7/1996 | Tockman et al. | 607/18 |
| 5,544,661 A | 8/1996 | Davis et al. | 128/700 |
| 5,549,650 A | 8/1996 | Bornzin et al. | 607/24 |
| 5,554,177 A | 9/1996 | Kieval et al. | 607/17 |
| 5,562,711 A | 10/1996 | Yerich et al. | 607/17 |
| 5,578,064 A | 11/1996 | Prutchi | 607/19 |
| 5,584,868 A | 12/1996 | Salo et al. | 607/17 |
| 5,609,612 A | 3/1997 | Plicchi et al. | 607/17 |
| 5,626,620 A | 5/1997 | Kieval et al. | 607/9 |
| 5,626,623 A | 5/1997 | Kieval et al. | 607/23 |
| 5,628,777 A | 5/1997 | Moberg et al. | 607/122 |
| 5,674,256 A | 10/1997 | Carlson | 607/17 |
| 5,690,689 A | 11/1997 | Sholder | 607/24 |
| 5,700,283 A | 12/1997 | Salo | 607/17 |
| 5,713,930 A | 2/1998 | van der Veen et al. | 607/25 |
| 5,713,933 A | 2/1998 | Condie et al. | 607/28 |
| 5,716,383 A | 2/1998 | Kieval et al. | 607/9 |
| 5,749,906 A | 5/1998 | Kieval et al. | 607/9 |
| 5,800,471 A | 9/1998 | Baumann | 607/25 |
| 5,836,975 A | 11/1998 | DeGroot | 607/5 |
| 5,836,987 A | 11/1998 | Baumann et al. | 607/17 |
| 5,891,176 A | 4/1999 | Bornzin | 607/18 |
| 6,058,329 A | 5/2000 | Salo et al. | 607/17 |
| 6,070,100 A | 5/2000 | Bakels et al. | 607/9 |
| 6,144,878 A | 11/2000 | Schroeppel et al. | 600/515 |
| 6,144,880 A | 11/2000 | Ding et al. | 607/23 |
| 6,208,901 B1 | 3/2001 | Hartung | 607/23 |
| 6,223,082 B1 | 4/2001 | Bakels et al. | 607/17 |
| 6,280,389 B1 | 8/2001 | Ding et al. | 600/485 |
| 6,311,089 B1 | 10/2001 | Mann et al. | 607/30 |
| 6,371,922 B1 | 4/2002 | Baumann et al. | 600/485 |
| 6,430,439 B1 | 8/2002 | Wentkowski et al. | 607/9 |
| 6,438,421 B1 | 8/2002 | Stahmann et al. | 607/9 |
| 6,449,510 B1 | 9/2002 | Albers et al. | 607/25 |
| 6,480,742 B2 | 11/2002 | Stahmann et al. | 607/27 |
| 6,491,639 B1 | 12/2002 | Turcott | 600/508 |
| 6,507,756 B1 | 1/2003 | Heynen et al. | 607/9 |
| 6,512,952 B2 | 1/2003 | Stahmann et al. | 607/9 |
| 6,522,921 B2 | 2/2003 | Stahmann et al. | 607/9 |
| 6,522,923 B1 | 2/2003 | Turcott | 607/27 |
| 6,553,258 B2 | 4/2003 | Stahmann et al. | 607/9 |
| 6,597,951 B2 | 7/2003 | Kramer et al. | 607/9 |
| 6,665,564 B2 | 12/2003 | Lincoln et al. | 607/17 |
| 6,832,113 B2 * | 12/2004 | Belalcazar | 607/23 |
| 6,963,777 B2 * | 11/2005 | Lincoln et al. | 607/18 |
| 7,206,636 B1 * | 4/2007 | Turcott | 607/17 |
| 2001/0047194 A1 | 11/2001 | Thompson et al. | 607/59 |
| 2002/0133198 A1 | 9/2002 | Kramer et al. | 607/9 |
| 2002/0143264 A1 | 10/2002 | Ding et al. | 600/510 |
| 2003/0097158 A1 | 5/2003 | Belalcazar | 607/32 |
| 2003/0105496 A1 | 6/2003 | Yu et al. | 607/17 |
| 2003/0199936 A1 | 10/2003 | Struble et al. | 607/25 |
| 2004/0193223 A1 | 9/2004 | Kramer et al. | |
| 2006/0009818 A1 | 1/2006 | Von Arx et al. | |
| 2007/0150014 A1 | 6/2007 | Kramer et al. | |

FOREIGN PATENT DOCUMENTS

| | | |
|---|---|---|
| EP | 0474958 | 3/1992 |
| EP | 0793975 | 9/1997 |
| WO | WO-2006008535 A1 | 1/2006 |

OTHER PUBLICATIONS

"Noninvasive MIKRO-TIP Pulse Pressure Transducer Model SPT-301", *Millar Instruments, Inc., Product Information*, (2000), 1 pg.

Adolph, Robert J., et al., "Prolongation of Isovolumic Contraction Time in Left Bundle Branch Block", *American Heart Journal*, 78, (1969),585-591.

Cazeau, S. , et al., "Multisite stimulation of correction of cardiac asynchrony", *Heart*, 84, (2000),579-581.

Cha, Karen , et al., "Pulsus Alternans", *The New England Journal of Medicine*, vol. 334, No. 13, (Mar. 28, 1996),834.

Duncan, Sr., Alison M., et al., "The Effect of Biventricular Pacing on Ejection and Filling Hemodynamics in Dilated Cardiomyopathy Patients With Activation Disturbances: the MUSTIC Study", *JACC, Abstracts Poster Session 1167-56*, (2001), 1 pg.

Hirschfeld, Stephen , et al., "The isovolumic contraction time of the left ventricle. An echographic study", *Circulation*, 54(5), (Nov. 1976),751-756.

Kass, David A., "Improved Left Ventricular Mechanics From Acute VDD Pacing in Patients with Dilated Cardiomyopathy and Ventricular Conduction Delay", *Circulation*, 99(12), (Mar. 30, 1999),1567-1573.

Kostis, J. B., "Mechanisms of heart sounds", *American Heart Journal*, 89(4), Letter to the Editor,(Apr. 1975),546-547.

Kramer, Andrew P., "Automatic Selection From Multiple Cardiac Optimization Protocols", U.S. Appl. No. 10/624,458, filed Jul. 21, 2003, 49.

Lab, M , et al., "Pulsus Alternans", *Cardiovascular Research*, vol. 27, No. 8, (Aug. 1993),1407-1412.

Leonelli, F. M., et al., "Systolic and Diastolic Effects of Variable Atrioventricular Delay in Patients With Complete Heart Block and Normal Ventricular Function", *The American Journal of Cardiology*, 80(3), (Aug. 1997),294-298.

Lincoln, William C., "Cardiac Rhythm Management System and Method Using Time Between Mitral Valve Closure and Aortic Ejection", U.S. Appl. No. 10/099,865, filed Mar. 13, 2002, 33.

Little, William C., "The Left Ventricular dP/dtmax-End-Diastolic Volume Relation in Closed-Chest Dogs", *Circulation Research*, 56, (1985),808-815.

Littmann, L. , et al., "Apparent Bigeminy and Pulsus Alternans in Intermittent Left Bundle-Branch Block", *Clin. Cardiol.*, vol. 22, (Jul. 1999),490.

McIntyre, K. M., et al., "A Noninvasive Method of Predicting Pulmonary-Capillary Wedge Pressure", *The New England Journal of Medicine*, vol. 327, No. 24, (Dec. 10, 1992),1715-1720.

McLaughline, David P., et al., "Pulsus Alternans", *The New England Journal of Medicine*, vol. 341, No. 13, (Sep. 23, 1999),955.

Ritter, P. , et al., "A Built-In System Based on the Peak Endocardial Acceleration (PEA) for AV-Delay Optimization in DDDR Pacing", *Pace—Pacing and Clinical Electrophysiology*, No. 5, Futura Publishing Company, Inc.,(May 1997),1567.

Ritter, P. , et al., "Determination of the optimal atrioventricular delay in DDD pacing. Comparison between echo and peak endocardial acceleration measurements", *Europace*, 1(2), (Apr. 1999),126-130.

Ritter, P. , et al., "New Method for Determining the Optimal Atrio-Ventricular Delay in Patients Paces in DDD Mode for Complete Atrio-Ventricular Block", *Pace*, 18, Abstract No. 237, (Apr. 1995),855.

Spodick, D H., et al., "Isovolumetric contraction period of the left ventricle. Results in a normal series and comparison of methods of calculation by atraumatic techniques", *American Heart Journal*, 76(4), (Oct. 1968),498-503.

Surawicz, B. , et al., "Cardiac Alternans: Diverse Mechanisms and Clinical Manifestations", *JACC*, vol. 20, No. 2, (Aug. 1992),483-499.

Tei, C., et al., "New index of combined systolic and diastolic myocardial performance: a simple and reproducible measure of cardiac function—a study in normals and dilated cardiomyopathy", *Journal of Cardiology*, 26(6), (Dec. 1995),357-66.

Waider, W., et al., "First heart sound and ejection sounds. Echocardiographic and phonocardiographic correlation with valvular events", *The American Journal of Cardiology*, 35(3, (Mar. 1975),346-356.

Weissler, A. M., "Systolic Time Intervals in Heart Failure in Man", *Circulation*, 37, (1968),149-159.

Yu, Yinghong, et al., "Method and Apparatus for Optimizing Ventricular Synchrony During DDD Resynchronization Therapy Using Adjustable Atrio-Ventricular Delays", U.S. App. No. 11/463,176, filed Aug. 8, 2006, 45 Pages.

"U.S. Appl. No. 09/993,351, Amendment and Response filed Apr. 12, 2004 to Non-Final Office Action mailed Jan. 12, 2004", 18 pgs.

"U.S. Appl. No. 09/993,351, Amendment Under 37 CFR Sec. 1.312(a) filed Sep. 2, 2004 to Notice of Allowance mailed Jun. 2, 2004", 13 pgs.

"U.S. Appl. No. 09/993,351, Non-Final Office Action mailed Jan. 12, 2004", 9 pgs.

"U.S. Appl. No. 09/993,351, Notice of Allowance mailed Jun. 2, 2004", 7 pgs.

"U.S. Appl. No. 09/993,351, Response to Rule 312 Communication mailed Oct. 12, 2004", 2 pgs.

"U.S. Appl. No. 09/993,351, Supplemental Notice of Allowability mailed Aug. 30, 2004", 4 pgs.

"Written Opinion for corresponding PCT Application No. PCT/US2006/044160", (Mar. 14, 2007),7 pgs.

* cited by examiner

NON-INVASIVE METHOD AND APPARATUS FOR CARDIAC PACEMAKER PACING PARAMETER OPTIMIZATION AND MONITORING OF CARDIAC DYSFUNCTION

CROSS-REFERENCE TO RELATED APPLICATION

This application is a continuation of U.S. patent application Ser. No. 09/993,351, filed on Nov. 16, 2001, now issued as U.S. Pat. No. 6,832,113, the specification of which is incorporated herein by reference.

FIELD OF THE INVENTION

The present invention pertains generally to medical devices and more particularly to medical devices for monitoring activity of the heart and providing therapy thereto including implantable cardiac pacemakers and external programmers and other devices for determining optimal pacing parameters for such implantable pacemakers and for providing such pacing parameters to an implanted device.

BACKGROUND OF THE INVENTION

Various types of medical devices are employed to monitor electrical or other activity of the heart and to provide therapy to the heart for the correction of electrical conduction defects, inadequate pump function, or irregular cardiac rhythms. Such defects and irregular rhythms may result from or indicate various pathological conditions of the heart, including congestive heart failure. Many such devices are implantable beneath the skin of a patient, i.e., in the patient's chest. Such implantable devices include a hermetically sealed canister containing electronic circuitry for implementing the functions of the device, one or more electrodes implanted in one or more of the ventricles and/or atria of the heart, or in close proximity thereto, and leads for connecting the electrodes to the circuitry within the device canister. The device circuitry includes circuitry for detecting electrical signals produced by the heart, which signals are picked up at the electrodes, along with circuitry, typically implemented in a microprocessor, for analyzing the thus detected cardiac signals. The device may also include circuitry for providing therapy in the form of electrical signals applied to the heart. Such signals are provided to the heart via the leads and electrodes mounted in the heart so as to correct electrical conduction defects or abnormal rhythms. The analysis circuitry controls the delivery of such electrical therapy signals based on the detected cardiac activity signals. The implantable device may also include a transmitter/receiver for transmitting cardiac activity and other information to an external device for, e.g., storage and/or further analysis, and for receiving information, such as programming instructions, from the external device via, for example, an RF link.

An example of such an implantable cardiac device is an implantable cardiac pacemaker. A pacemaker provides relatively low-level electrical pulses to the heart to stimulate heart activity when the natural cardiac rate provided by the heart is too low. A dual chamber pacemaker includes electrodes positioned in both the atria and ventricles of the heart for detecting naturally occurring atrial and ventricular activations, and for providing pacing pulses to the atria and/or ventricles as needed. Such a device monitors the time between sensed and paced atrial and ventricular activations and provides pacing pulses as needed to maintain an adequate heart rate. For example, such a device will note the occurrence of a sensed or paced atrial or ventricular event and, if a subsequent naturally occurring atrial and/or ventricular event is not sensed within a certain time (escape interval) following the first sensed or paced event, a pacing pulse will be applied to the atria and/or ventricles to maintain a desired heart rate.

Implantable cardiac pacemakers may also be employed to improve cardiac function in heart failure patients. Such implantable pacemakers may improve cardiac pump function by correcting left ventricular conduction system defects. In such systems an electrical pacing signal is provided by the pacemaker to a pacing lead implanted epicardially in the coronary vein to stimulate the left ventricle. Biventricular pacing may also be provided. Such heart failure therapy is commonly referred to as cardiac resynchronization therapy. Implantable pacemakers for heart failure therapy may be implemented as dual or triple chamber pacemakers. Such pacemakers may be included within an implantable device capable also of providing atrial and/or ventricular defibrillation.

As discussed above, left ventricular or biventricular pacing can have a beneficial effect for patients suffering from congestive heart failure. However, it has been found that the various parameters which control such pacing must be set within a certain range for such pacing to have a beneficial effect for those patients, or to yield the best therapeutic response. For example, it has been found that patients exhibiting congestive heart failure have a specific range or value of AV delay (the maximum time allowed to pass following a sensed or paced atrial event before the ventricles are paced), over which the therapeutic response to pacing is positive. Also, within the range of AV delay, or other pacemaker settings, for which a positive therapeutic effect is provided by pacing, is a more narrow optimum subrange of AV delay or other pacing parameter values which provide the greatest degree of therapeutic improvement. Arbitrarily setting the AV delay and other pacing parameters at nominal values may not guarantee the optimum benefit obtainable (or even any benefit at all) by left ventricular or biventricular pacing in congestive heart failure patients. It would, therefore, be advantageous to have a system which allows an operator to determine whether a controlled pacing parameter or set of parameters is optimal for a given patient and, if not, which allows the operator to reprogram an implanted pacemaker such that the implanted device is made to operate in a pacing mode and with pacing parameters that result in an optimum benefit to the patient.

U.S. Pat. No. 5,540,727 to Tockman, et al. describes a method and apparatus for optimizing the pacing mode and pacing cycle parameters of an implanted dual chamber pacemaker. This patent describes providing as inputs to an external monitor/programming device data from one or more cardiac performance monitoring devices. Such devices may include external equipment, such as an acceleration sensor, capable of providing signals characteristic of features of the mechanical movements of the heart muscle, its valves, and the blood being pumped by it, a Doppler flow sensor for sensing cardiac output, a pressure cuff or similar type sensor for providing an indication of mean arterial pressure, a pulse oximeter to provide signals corresponding to the percentage concentration of oxygen and carbon dioxide in the patient's blood, and/or a respiration sensor capable of analyzing respiratory gases and delivering signals proportional thereto to the monitor/programmer. One or more sensors may also, or alternatively, be implanted within the body to sense various cardiac performance parameters and to provide corresponding data to the monitor/programmer.

Data from the cardiac performance monitoring devices is used by the monitor/programmer to monitor one or more physiological parameters during a pacing interval with a given pacing parameter (e.g., AV delay) set at a given value and with a given pacing mode. The selected pacing parameter is changed incrementally, and monitoring of the detected physiological parameters is repeated at each increment of the pacing parameter. Between each such pacing period, the heart is allowed to beat at a natural sinus rhythm, in order to establish a baseline for comparison. The physiological parameters monitored during each pacing interval are analyzed to determine the selected pacing parameter value and pacing mode which results in the best resulting physiological response, which could be either a maximum or minimum value of a physiological parameter, depending upon the particular physiological parameter involved. An implanted pacemaker is then programmed using the external programmer to operate with the pacing parameter value and pacing mode associated with the best determined physiological parameter response.

A known method of evaluating heart mechanical performance is described in U.S. Pat. No. 5,291,895 to McIntyre. This patent describes a system for evaluating cardiac performance which employs a finger pressure sensor including a piezoelectric pulse pickup and an inflatable cuff which wraps around a patient's finger to apply pressure, through the pickup, to the skin of the patient's finger. Pressure pulses detected using the finger sensor may be analyzed to detect abnormal cardiac performance. In particular, abnormal cardiac performance may be identified by analyzing the finger pressure signal obtained during and after an activity which produces stress on the patient's heart. An example of such a heart-straining activity is the Valsalva maneuver, in which a patient exhales forcefully into a closed system so as to maintain an increased intrathoracic pressure for a short period of time. It has been determined that the reflected arterial-pulse contour detected from a patient's finger during the Valsalva maneuver is predictive of pulmonary-capillary wedge pressure. In particular, the pulse-amplitude ratio of the final (minimal) to initial (maximal) amplitude of the strain phase of the maneuver has been determined to correlate well to pulmonary-capillary wedge pressure. Pulmonary-capillary wedge pressure is a well-known measure of heart failure disease.

What is desired is a system and method which allows a physician to easily, accurately, and noninvasively monitor the condition of a heart failure patient and to optimize the pacing parameters of an implanted pacemaker used to treat such a condition. In particular, what is desired is a system and method which allows a physician to monitor the condition of a heart failure patient and to optimize the pacing parameters in an implanted pacemaker providing therapy to the patient by noninvasively monitoring a physiological parameter related to heart performance and programming the implanted device to optimize such a parameter.

SUMMARY OF THE INVENTION

The present invention provides a method and apparatus for monitoring the condition of a heart failure patient and for determining optimal pacing parameters for an implanted cardiac pacemaker based on noninvasive monitoring of physiological parameters related to heart performance. In particular, the present invention features an external programmer device for monitoring the progression of heart failure disease in a patient and/or transmitting programming instructions to a pacemaker device implanted in the patient to optimize one or more pacing parameters thereof. A finger sensor, such as a photoplethysmogram detector, is provided, which may be clipped to the tip of a finger of a patient in which a pacemaker is implanted. The finger sensor is coupled to the external programmer device to provide a plethysmogram signal thereto. The finger plethysmogram signal is analyzed using the external programmer device to determine and monitor cardiac performance from characteristics thereof. The external programmer device may be employed to program one or more pacing parameters (e.g., the AV delay, the pacing chambers, etc.) in the implanted device, such that the performance of the heart, as indicated from the detected finger plethysmogram signal, is optimized. Cardiac performance parameters monitored via the finger plethysmogram signal in accordance with the present invention also may be employed to determine the optimum location for the placement of cardiac pacing electrodes at the time of implant.

Various physiological characteristics may be non-invasively monitored, e.g., using a finger plethysmogram signal, analyzed to determine cardiac performance and, in turn, used to optimize implanted cardiac pacemaker device pacing parameters in accordance with the present invention. For example, heart failure patients with advanced ventricular dysfunction often exhibit pulsus alternans, i.e., pressure pulses that alternate in amplitude: strong, weak, strong, weak. Pulsus alternans can be observed non-invasively, e.g., using the finger plethysmogram, and the progression of heart failure monitored by observing the presence of pulsus alternans in the finger plethysmogram signal provided to an external programmer device. The external programmer device may be used to adjust the pacing parameters of an implanted pacemaker to minimize the pulsus alternans as non-invasively identified, e.g., in the finger plethysmogram signal.

Atrial fibrillation patients experience irregular beat-to-beat blood pressure changes. Such pressure changes may be non-invasively identified, e.g., from a finger plethysmogram signal. A finger plethysmogram signal may thus be used by an operator of an external programmer device, in accordance with the present invention, to monitor the progression of heart failure and to adjust an implanted pacemaker is pacing parameters such that the blood pressure of the atrial fibrillation patient is regularized, resulting in a plethysmogram signal with more uniform peak amplitudes. Such plethysmogram information could also be combined with ventricular rate information to optimize the pacing parameters of a pacemaker implanted in an atrial fibrillation patient.

A finger plethysmogram signal provided to an external programmer device in accordance with the present invention may also be used to monitor filling pressures, such as pulmonary-capillary wedge pressure, which is a common measure of a patient's hemodynamics that is an approximation to the left ventricular diastolic end pressure. As discussed above, pulmonary-capillary wedge pressure (filling pressure) is a well-known measure of heart failure disease. In accordance with the present invention, pulmonary-capillary wedge pressure (filling pressure) may be monitored non-invasively, e.g., using a finger plethysmogram signal or other blood pressure related signal obtained during the performance of a classic Valsalva maneuver by a patient. Performance of the Valsalva maneuver may preferably be monitored by the external programmer device to which a finger plethysmogram signal is provided. For this purpose, a mouthpiece may be provided coupled to the external programmer device, and a pressure sensor providing a pressure signal to the programmer device coupled to the mouthpiece for determining the patient's intrathoracic pressure during performance of the Valsalva maneuver. The intrathoracic pressure signal may be employed by the external programmer device for monitoring the patient's performance of the Valsalva maneuver. An external programmer device in accordance with the present invention may employ the finger plethysmogram signal generated during the Valsalva maneuver to monitor the progression of heart failure in a patient, either by qualitative observation of the shape of the finger plethysmogram signal during performance of the Valsalva maneuver or by quantitative estimate of filling pressure derived therefrom in a conventional manner. The external programmer device may be employed to program one or more pacing parameter of a pacemaker implanted in a patient in a manner such that the finger plethysmogram signal generated during the Valsalva maneuver is made more normal, i.e., the qualitative shape of the finger plethysmogram signal is more normal or the quantitative pulmonary-capillary wedge pressure (filling pressure) estimated therefrom is minimized.

Various different procedures may be employed for optimizing the pacing parameters of an implanted pacemaker in accordance with the present invention, depending upon the cardiac performance parameters non-invasively monitored, e.g., using a finger plethysmogram signal provided to an external programmer device. For example, if the finger plethysmogram signal is employed to monitor filling pressure (either qualitatively or quantitatively), a clinician may employ the present invention to monitor and store the plethysmogram signal obtained from a patient performing the Valsalva maneuver for a given set of pacemaker pacing parameters, and then send the patient home. After a few days, needed to reach a steady state fluid balance, the patient would return, a finger plethysmogram obtained while the patient performed the Valsalva maneuver again, and further adjustments to the pacemaker pacing parameters made using the external programmer device, as necessary. After several such trials, the optimum pacing parameters to be programmed into the pacemaker device may be selected as those yielding the best finger plethysmogram response during the Valsalva maneuver, e.g., the parameters yielding the best pulmonary-capillary wedge pressure. The Valsalva response in the finger plethysmogram signal may also be observed, and/or the pulmonary-capillary wedge pressure derived therefrom, using a programmer device in accordance with the present invention, for monitoring disease progression of a patient, so that a deterioration can be better detected and characterized. Such monitoring may result in a determination that the patient's disease may be managed more thoroughly with therapies other than, or in addition to, cardiac pacing.

Optimum pacing parameters may be determined, e.g., automatically using the external programmer device in a single diagnostic session. For example, the external programmer device may control an implanted pacemaker to pace a patient's heart using a series of different pacing parameter values. The resulting finger plethysmogram signal obtained during each such pacing interval may be analyzed and stored. Between each such pacing interval, the heart may be allowed to beat at a natural sinus rhythm, in order to establish a baseline for comparison. Baseline beat amplitudes and repeated pacing intervals for each pacing parameter value under test may be employed in the determination of the cardiac effect of pacing as reflected in the finger plethysmogram signal, such that the effects of noncardiogenic changes on finger pulse amplitude and other artifacts are rejected. After cycling through various pacing parameters in this manner, the resulting finger plethysmogram signals stored may be analyzed, and the implanted pacemaker programmed either manually or automatically with the pacing parameters resulting in the plethysmogram signal indicating the best cardiac performance, e.g., the finger plethysmogram signal indicating the largest pulse amplitude response, eliminated or reduced pulsus alternans, or, in the case of a patient with atrial fibrillation, the finger plethysmogram signal with the most uniform peak amplitudes, i.e., indicating reduced irregular pressure changes.

A system and method in accordance with the present invention may be used to optimize any of several different pacing parameters to optimize pacemaker performance. Such parameters may include, for example, the AV delay, pacing mode, pacing power (e.g., pacing pulse amplitude and/or pulse width) and/or pacing location (left and/or right ventricle). In general, the present invention may be used to optimize any programmable pacing parameter which would result in a hemodynamic response. A system and method in accordance with the present invention also may be employed in the manner described to determine the optimum location for the placement of cardiac pacing electrodes at the time of implant.

Further objects, features, and advantages of the invention will be apparent from the following detailed description, taken in conjunction with the accompanying drawings.

DETAILED DESCRIPTION OF THE INVENTION

Figure 1:
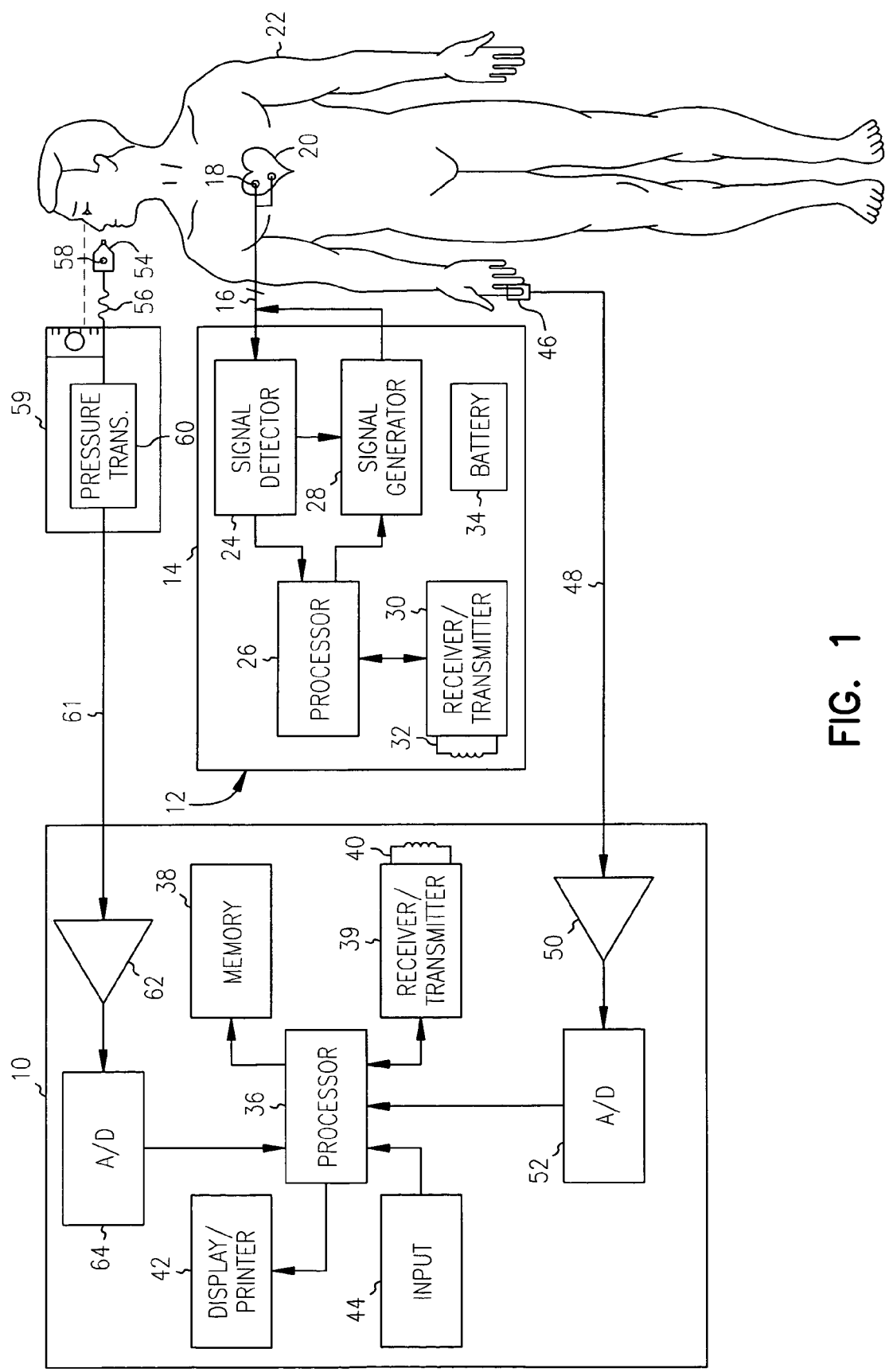
FIG. 1 is a schematic diagram of an exemplary system in accordance with the present invention for monitoring cardiac disease progression and/or for optimizing the pacing parameters of a pacemaker implanted in a patient using a noninvasive plethysmogram signal obtained using a finger sensor and a pacemaker programmer.

An exemplary system in accordance with the present invention for monitoring cardiac disease progression and for optimizing the pacing parameters of an implanted pacing device using cardiac performance information obtained from a noninvasive sensor is illustrated in, and will be described in detail with reference to, FIG. 1. A system in accordance with the present invention is preferably embodied in an external programmer device 10. The external programmer device 10 is employed to monitor cardiac disease progression and/or to program the operating parameters of an implantable cardiac device 12.

The implantable cardiac device 12 includes a hermetically sealed canister 14 which encloses circuitry for detecting and analyzing cardiac electrical conduction defects and arrhythmias and for providing therapy therefore. The circuitry within the canister 14 is connected via one or more leads 16 to one or more electrodes 18 which are implanted in or near the chambers of a patient's heart 20. Depending upon the specific application and functionality of the implantable cardiac device 12, electrodes 18 may be positioned in or near the ventricles, atria, or, preferably, both the atria and ventricles of the heart 20. The electrodes 18 pick up electrical signals produced in the chambers of the heart 20 and provide electrical contact for electrical pulses or shocks which are delivered to the chambers of the heart 20 to pace or defibrillate/cardiovert the heart 20. In a dual chamber pacemaker, for example, electrodes 18 are positioned in or near both the atria and ventricles of the heart 20 to detect atrial and ventricular activity of the heart 20 and to provide pacing pulses to the atria and ventricles. A plurality of leads 16 may be required to connect the electrodes 18 positioned in or near the heart 20 to the circuitry within the device canister 14. As is known in the art, multiple electrodes 18 may be coupled to the circuitry within the canister 14 via a single one of the leads 16. The canister 14, leads 16, and electrodes 18 are preferably designed such that the entire device 12 is implantable beneath the skin of a patient 22.

The leads 16 connect the electrodes 18 positioned within or near the heart 20 to signal detection circuitry 24 within the implantable device canister 14. The signal detection circuitry 24 may be implemented in a conventional manner to provide atrial and/or ventricular activity signals based on the cardiac signals picked up at the electrodes 18. Conventional signal detection circuitry 24 may include signal amplifiers and filters, and may include, in addition, circuitry for detecting atrial and ventricular depolarizations and for providing atrial and ventricular depolarization detection signals in response thereto.

The signals provided by the signal detection circuitry 24 are provided to an implantable device system processor 26. The implantable device system processor 26 may be implemented, for example, as one or more conventional microprocessors with associated memory. Memory may be an integral part of, or separate from, but coupled to, the processor 26. Memory is employed in a conventional manner to store data, such as cardiac activity data, for analysis by the processor 26, as well as to store the programming instructions which control the functions performed by the processor 26. For example, such programming instructions may include various pacing parameters, which are used to control pacing of the heart 20, and which are programmable from external to the patient 22 by use of the external programmer device 10 in a manner to be described in more detail below. Of course, other general and conventional programming instructions for the processor 26 may also be stored in memory.

The implantable cardiac device 12 preferably also includes signal generator circuitry 28 for implementing a dual or triple chamber or other pacemaker function. The signal generator circuitry 28 operates in a conventional manner to provide pacing pulses to the electrodes 18 positioned in the heart 20 via the leads 16 to maintain a desired cardiac rate or, in general, to improve cardiac performance. The signal generator 28 preferably receives atrial and ventricular depolarization detection signals directly from the signal detection circuitry 24. The signal generator circuitry 28 employs the atrial and ventricular depolarization detection signals from the signal detection circuitry 24 in a conventional manner to, for example, inhibit atrial or ventricular pacing when timely naturally occurring atrial or ventricular depolarizations are detected. The signal generator 28 may be controlled in a conventional manner, e.g., by the implantable device processor 26 and/or internally, to provide, e.g., conventional dual chamber bradycardia or other pacing.

The signal generator circuitry 28 may also include defibrillator/cardioverter circuitry for applying relatively high-level defibrillating or cardioverting electricity energy to the atria and/or ventricles of the heart 20 via the leads 16 and electrodes 18 positioned in the heart 20. The implantable device processor 26 monitors the atrial and ventricular activity signals provided thereto by the signal detector circuitry 24. Conventional algorithms known in the art may be used to determine the occurrence of atrial or ventricular fibrillation from such signals. If such a cardiac arrhythmia is detected, the implantable device processor 26 may control the signal generator 28 to provide relatively high-level electrical shocks to the ventricles and/or atria to defibrillate and/or cardiovert the heart 20 in a conventional manner. It should be understood, however, that the present invention is particularly applicable to optimizing pacing parameters and, therefore, the present invention is particularly applicable to pacemaker devices which need not, but may, include defibrillator/cardioverter circuitry.

The implantable cardiac device 12 includes a receiver/transmitter 30 including an antenna coil 32. The receiver/transmitter 30 may be implemented in a conventional manner to transmit data from the implantable device processor 26 out of the implantable device 12 to the external programmer device 10. For example, cardiac activity data detected by the signal detector circuitry 24 may be transmitted to the programmer device 10 to be stored and analyzed therein in more detail than is possible in the implanted device 12 itself. The receiver/transmitter 30 may also receive programming instructions from the programmer device 10 for, for example, reprogramming operating parameters of the implantable cardiac device 12 to optimize pacing parameters thereof in accordance with the present invention. Communication between the receiver/transmitter 32 and the programmer device 10 may be implemented in a conventional manner e.g., via an RF link.

The implantable cardiac device 12 also includes a battery 34, which provides power for the processor 26 and other circuit components of the implantable cardiac device 12.

The circuitry for implementing the signal detector 24, processor 26, signal generator 28, receiver/transmitter 30 and other functions of the implantable cardiac device 14 may be implemented in a conventional manner using analog or digital circuitry, including one or more microprocessors, or any combination thereof. As will be known to those skilled in the art, functions performed by the signal detector 24, signal generator 28, and receiver/transmitter 30 may be performed by independent analog and/or digital circuitry, as suggested by the illustration of FIG. 1, or may be implemented in one or more processors 26, or any combination of independent circuits and one or more processors.

The external programmer device, 10 includes a programmer processor 36. The programmer processor 36 may be programmed in a conventional manner to perform the functions of the programmer device 10 as described herein. Programming instructions for the processor 36 may be stored in programmer memory 38 associated with the processor 36. The programmer memory 38 may be implemented in a conventional manner as part of or separate from the processor 36. In addition to programming instructions, memory 38 is preferably also employed to store physiological parameters related to cardiac performance which are obtained by the programmer 10 from a patient 22 by a noninvasive measurement technique, as will be described in more detail below. Memory 38 may also be employed to store cardiac or other information received by the programmer device 10 from the implanted device 12.

The external programmer device 10 includes a receiver/transmitter 39, including an antenna coil 40. The receiver/transmitter 39 may be implemented in a conventional manner to transmit instructions from the programmer device 10 to the implanted device 12, and to receive data from the implanted device 12. Of course, the receiver/transmitter 39 employed in the programmer device 10 must be compatible with the receiver/transmitter 30 in the implanted device 12. As discussed above, communication between the receiver/transmitter 39 in the programmer device 10 and the receiver/transmitter 30 in the implanted device 12 may be implemented in a conventional manner, e.g., via an RF link. The programmer receiver/transmitter 39 and/or the antenna 40 of the programmer receiver/transmitter 39 may, but need not, be mounted in a small hand-held portable wand or other structure which is connected via a cable to the programmer device 10 in a conventional manner. This conventional wand structure allows the receiver/transmitter 39 and/or the antenna 40 to be positioned on or near a patient 22 close to the position of the device 12 as implanted in the patient, thereby facilitating low power communication between the receiver/transmitter 39 in the programmer 10 and the receiver/transmitter 30 in the implanted device 12.

The programmer processor 36 is also preferably coupled to a programmer display 42 and a programmer input device 44. The display 42 may be implemented in a conventional manner as a CRT or other type of graphic display, and/or may include a printer capability for hard copy output. The programmer processor 36 controls the display 42 in a conventional manner to display various types of programmer information thereon, including user interface information which facilitates use of the programmer 10 by a physician, and physiological and/or cardiac parameter data obtained by the programmer 10 from a noninvasive physiological parameter sensor and/or transmitted to the programmer 10 from the implanted device 12. The input device 44 may be implemented in a conventional manner, such as using a conventional keyboard, mouse, track ball, light pen, etc., or any combination of such input devices.

In accordance with the present invention, the programmer device 10 receives as an input thereto a finger plethysmogram signal. The finger plethysmogram signal may be provided to the programmer 10 using a plethysmogram detector 46 which, preferably, clips onto a finger of the patient 22. The finger clip plethysmogram signal detector 46 may preferably be implemented using a conventional pulse oximeter finger clip sensor which provides a finger photoplethysmogram signal on a line 48 to the programmer device 10. A pulse oximeter finger clip sensor is a photoelectric device which provides a photoplethysmogram by illuminating the finger tip with a light emitting diode and sampling the light transmitted through the finger with a photodetector. The light transmitted through the vascular bed of the finger tip reflects arterial pulsation at the finger tip, which, in turn, is a reflection of aortic pulsation. The finger plethysmogram signal provided by the finger detector 46 on line 48 is preferably amplified and filtered, e.g., by conventional amplifier/filter circuitry 50, and converted, by a conventional analog-to-digital converter 52, into a digital finger plethysmogram signal which is provided to the programmer processor 36 for analysis. It should be noted that the amplifier/filter circuitry 50 may be implemented in a conventional manner in whole or in part within the programmer device 10 and/or in the finger detector 46 itself, or imbedded in a connector of the finger detector cable 48. The analog-to-digital converter 52 may be implemented in a conventional manner as part of or separate from the programmer processor 36. The finger plethysmogram signal obtained by the programmer processor 36 from the finger detector 46 may be displayed to an operator on the programmer device display 42.

It should be understood that plethysmogram signal detectors other than conventional pulse oximeter finger clip sensors may be employed to provide plethysmogram signals for use in accordance with the present invention. For example, a finger clip detector which includes a piezoelectric pulse pickup sensor which is pressed against a patient's finger by a spring force, a pneumatic occlusive air cuff sensor, or an impedance plethysmogram sensor (which passes current through the finger and, by monitoring impedance changes, obtains the pulse arterial waveform), might also be used. However, piezo and cuff sensors are much more cumbersome to use than the preferred photoplethysmogram sensors. Furthermore, other types of plethysmogram or pressure signal detectors placed at sites on the patient other than the patient's finger may be employed to provide plethysmogram or pressure signals for use in accordance with the present invention. For example, a tonometer sensor which employs the published and known concept of arterial tonometry to noninvasively obtain pulse waveforms may be used to provide pressure signals to a programmer device in accordance with the present invention. Such a device is placed on the patient's forearm, over the radial artery. A tonometer may provide better quality signals than a pulse oximeter finger clip sensor, but the finger clip sensor is easier to use. Other possible sites for use of a photoplethysmogram sensor are the earlobe sensor and the reflectance forehead sensor. A nasal bridge sensor may also provide an arterial pulsation signal that may be used in the present invention. A thoracic impedance technique, in which current is passed through the thorax via external electrodes, could also be used to obtain a signal that would reflect aortic pulse pressure, and thus be used with the present invention. All of the arterial pulse monitoring techniques described in this paragraph are well known in the art of physiological monitoring.

It should be noted that photoplethysmograms, such as provided by pulse oximeter finger clip sensors, can be sensitive to autonomic interference. Therefore, in accordance with the present invention, signal filtering and analysis procedures are preferably employed to diminish autonomic interference. As will be described in more detail below, an analysis procedure is preferably employed in accordance with the present invention where short pacing sequences are interleaved with intrinsic baseline beats. By analyzing the photoplethysmogram provided by the finger detector 46 during the short pacing periods, autonomic vasoconstriction and vasodilation effects on the plethysmogram signal are small compared to the effects introduced by pacing the heart. This technique, in addition to filtering of plethysmogram amplitude wander by interpolation or high pass filtering, and by taking repeated measures, yields an accurate method to eliminate physiological interference and produces an accurate measure of central pressure changes introduced by pacing.

A finger plethysmogram signal obtained by the finger detector 46 is related to pulse pressure. Abnormal cardiac performance may be identified by analyzing the finger plethysmogram signal obtained during and after an activity which produces a stress on the patient's heart, such as the Valsalva maneuver. To obtain such cardiac performance information from the finger detector 46, therefore, a programmer 10 in accordance with the present invention is preferably also adapted to monitor a classic Valsalva maneuver which may be performed by a patient 22 while a finger plethysmogram signal from the finger detector 46 is obtained by the programmer 10. For example, a mouthpiece 54, coupled to the distal end of a short hose 56 which is closed at the proximal end thereof to define a confined volume, and formed with an aperture 58 to release expired air, may be provided. The mouthpiece 54 may be implemented in a conventional manner, and is preferably replaceable and disposable. The hose 56 is preferably also disposable or washable. The hose 56 couples the mouthpiece 54 to a patient feedback device 59. The feedback device 59 may include a conventional pneumatic system and visual indicator so that the patient may receive visual feedback on the strength of their Valsalva exertion into the mouthpiece, and adjust it to maintain the required pressure. Such a pneumatic system may include a plastic ball in a cylinder that rises with exhaled pressure to a certain calibrated mark. A pressure transducer 60 is coupled to the hose 56, and provides a pressure signal which is amplified and filtered, e.g., by a conventional amplifier/filter circuit 62, and converted, by a conventional analog-to-digital converter 64, into a digital signal representative of the pressure in the confined volume formed by the mouthpiece 54 and hose 56. The digital pressure signal is provided to the programmer processor 36. The pressure transducer 60 is preferably mounted in the feedback device 59 near the mouthpiece 54 and provides the pressure signal therefrom to the detector 10 via a cable 61. The amplifier/filter circuit 62 and analog-to-digital converter 64 may be implemented with discrete circuitry in the programmer 10, or in the feedback device 59. The functions of these circuits may, alternatively, be implemented, in whole or in part, by the programmer processor 36. The programmer processor 36 processes the digital pressure signal provided by the analog-to-digital converter 64, and may provide a graphical or other indication on the processor display 42 in response thereto which is representative of the pressure in the hose 56. Thus, the programmer 10 may be employed to monitor correct execution of the Valsalva maneuver by a patient 22.

To perform a Valsalva maneuver, a patient 22 exhales forcefully into the mouthpiece 54 so as to maintain an increased intrathoracic pressure for a short period of time. The Valsalva maneuver may be monitored using the programmer device 10 by displaying on the programmer display 42 a graphical or other indication of the pressure being maintained by the patient. A patient viewing the patient feedback device 59 is provided with visual feedback such that the patient 22 may maintain a sufficient intrathoracic pressure level for the desired period of time. Based on the pressure signal received by the programmer processor 36 via the pressure transducer 60, the processor 36 may provide on the programmer display 42 indications which allow a physician or medical technician to monitor the correct execution of the Valsalva maneuver and to provide verbal instructions to the patient 22 to start blowing into the mouthpiece 54, to blow harder, to blow not so hard, to keep blowing, and to stop blowing, thereby controlling the Valsalva maneuver. Of course, any method may be employed by the programmer device 10 to help control the Valsalva maneuver performed by a patient 22.

In accordance with the present invention, the programmer device 10 preferably monitors the finger plethysmogram signal provided by the finger detector 46 while a patient 22 performs a classic Valsalva maneuver by blowing into the mouthpiece 54. From the finger plethysmogram signal thus detected, the programmer device 10 derives a value which is an estimate of, or related to, the pulmonary capillary wedge pressure of the patient 22. (The programmer processor 36 may be programmed to perform this function.) Pulmonary capillary wedge pressure is a well-known measure of heart failure disease in general and, more specifically, of reduced cardiac performance. (Pulmonary capillary wedge pressure (PCWP) is a common measure of a patient's hemodynamics that is an approximation to the left ventricular end diastolic pressure (LVEDP). It is difficult in normal clinical practice to measure LVEDP directly (an aortic catheter is needed). Physicians therefore use a venous approach, with the so-called Swan Ganz catheter, and through the wedge technique at the pulmonary vessels they obtain the so-called PCWP, which is an indirect measure of LVEDP. A high LVEDP (or a high PCWP) indicates reduced cardiac performance. It may be proven that the estimates of PCWP described herein are, more accurately, estimates of LVEDP, which is preferable. Therefore, it should be understood that wherever the term "pulmonary capillary wedge pressure" is used in the description and claims of the present application, that term also refers generally to filling pressures including both PCWP and LVEDP.)

Cardiac performance may be improved by pacing the patient's heart 20, e.g., using the implantable cardiac device 12, which is programmed to provide pacing pulses using a desired pacing mode and pacing parameters. Improved cardiac performance should be reflected in the pulmonary capillary wedge pressure (filling pressure) as detected by the programmer device 10 based on the finger plethysmogram signal obtained during performance of the Valsalva maneuver. Thus, in accordance with the present invention, a programmer device 10 which is programmed to control a Valsalva maneuver while receiving a finger plethysmogram signal from a finger detector 46, and to derive a value related to pulmonary capillary wedge pressure therefrom, may be used to determine optimal pacing parameters to be employed by an implantable cardiac device 12 to improve cardiac performance, especially for patients with congestive heart failure. The programmer 10 may then be used to program the implantable device 12 with the thus determined optimal pacing parameters.

Figure 2:
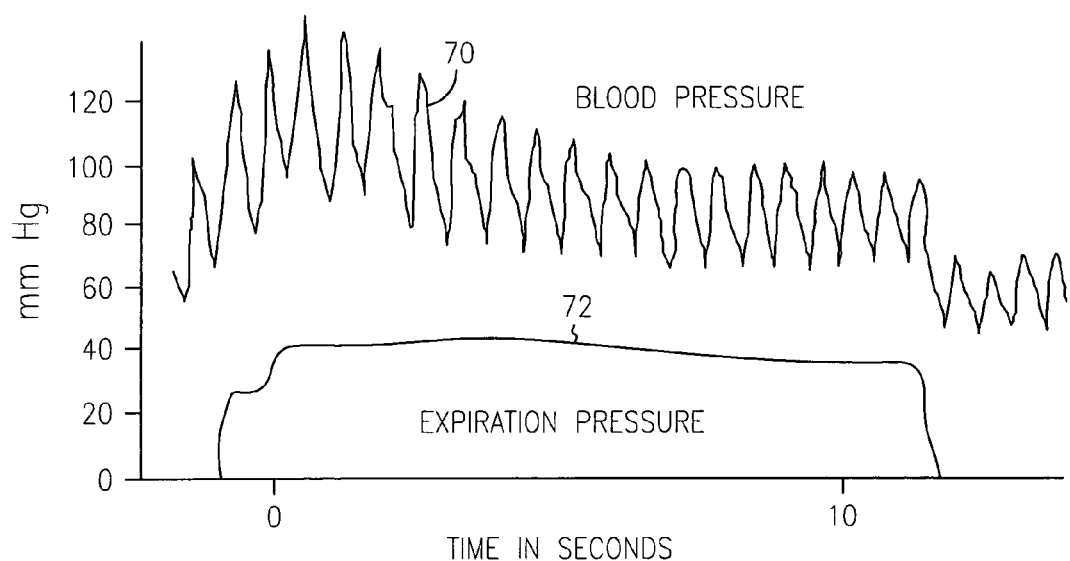
FIG. 2 is a waveform diagram showing the effect of the Valsalva maneuver on the blood pressure response in a normal subject.

The waveform diagram of FIG. 2 shows the normal arterial pressure response 70 of a patient during performance of the Valsalva maneuver. As shown, there is usually a fall in blood pressure during the "strain" phase of the Valsalva maneuver, as blowing pressure 72 is increased and maintained at a relatively high level. There is an increase in heart rate toward the end of the "strain" phase. There is an "overshoot" of arterial pressure shortly after release of the "strain" phase, accompanied by a depression in heart rate in the course of the "overshoot." There is fairly prompt return to near the baseline level of blood pressure, pulse pressure, and heart rate thereafter.

Figure 3:
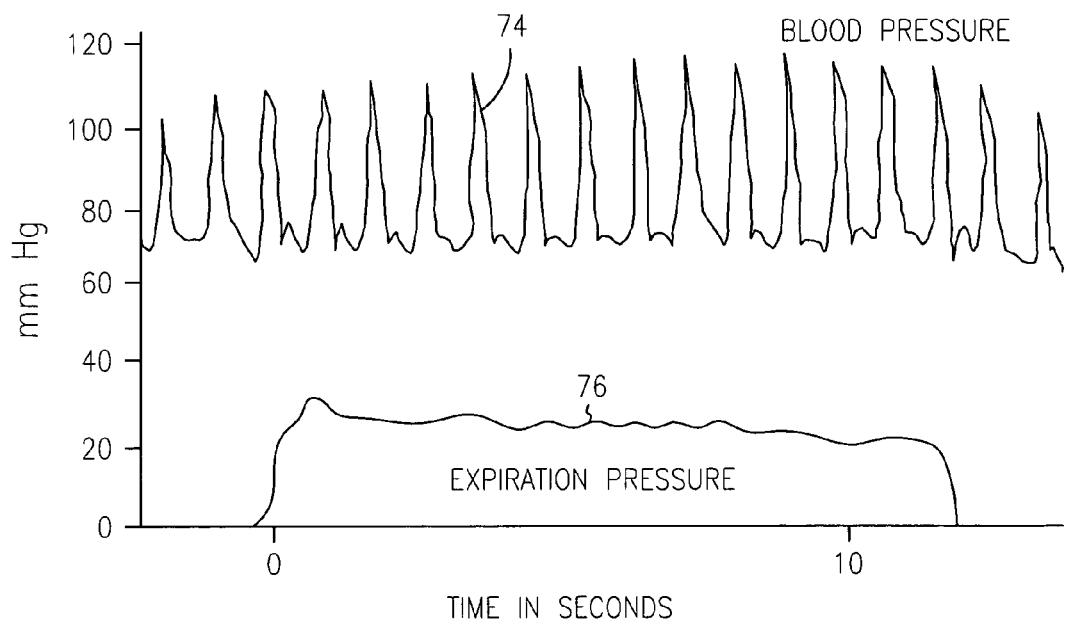
FIG. 3 is a waveform diagram showing the effect of the Valsalva maneuver on the blood pressure response in a patient with congestive heart failure.

In a patient with cardiac failure, the physiological response to the Valsalva maneuver is quite different. One characteristic response is called the "square wave" response, as shown in FIG. 3. This response involves a slight increase in blood pressure 74 with the initiation of the strain phase of the Valsalva maneuver, during which blowing pressure 76 is increased, and maintenance of nearly the same blood pressure, pulse pressure, and heart rate at this level throughout the "strain" phase. The "recovery" phase, which covers the release of the Valsalva maneuver "strain" phase, is characterized by the absence of any "overshoot," and the absence of recovery period cardiac slowing.

Thus, cardiac performance may be observed qualitatively by observing the arterial pressure signal produced during performance of the Valsalva maneuver by a patient 22. It has been found that arterial pressure is reflected in the finger plethysmogram signal obtained by a finger detector 46. Thus, qualitative cardiac performance may be observed noninvasively by monitoring the finger plethysmogram signal provided by a finger detector 46 and, e.g., displayed by a programmer device 10 on a display/printer 42, during performance of a Valsalva maneuver monitored by the programmer device 10, as described above. A more quantitative evaluation of cardiac performance may be obtained by calculating a value related to the pulmonary-capillary wedge pressure from the finger plethysmogram signal obtained by the programmer device 10 during performance of the controlled Valsalva maneuver. The programmer processor 36 may be programmed to employ any conventional known algorithm for calculating a value related to pulmonary-capillary wedge pressure from the finger plethysmogram signal. For example, it is known that the pulse-amplitude ratio of the final (minimal) to initial (maximal) amplitude of the pressure signal obtained during the strain phase of the Valsalva maneuver has been determined to correlate well to the pulmonary-capillary wedge pressure. Thus, by observing qualitative changes in the finger plethysmogram signal as displayed by the programmer device 10 on the programmer display 42, or changes in the quantitative value related to pulmonary-capillary wedge pressure as calculated from the finger plethysmogram signal by the programmer device 10, during performance of the Valsalva maneuver as controlled by the programmer device 10, during cardiac pacing using various different pacing modes and/or parameters by the implanted pacing device 12, optimum pacing parameters may be determined. Optimum pacing parameters are those parameters which result in a finger plethysmogram signal obtained during performance of the controlled Valsalva maneuver which corresponds most closely to a normal finger plethysmogram signal under such conditions, or which result in the best calculated value related to pulmonary-capillary wedge pressure.

An exemplary method for employing a programmer device 10 in accordance with the present invention to optimize the pacing parameters of a pacing device 12 implanted in a patient 22 based on a detected finger plethysmogram signal obtained during a programmer monitored Valsalva maneuver is as follows. A symptomatic congestive heart failure patient, or a patient suffering from another cardiac condition, and who has an implantable pacemaker device 12 implanted to treat the condition, or another condition, may be required to come to a pacemaker follow-up clinic. The patient 22 would sit or lie down in a resting position and have the finger clip detector 46 attached to his or her finger. The patient 22 would then blow into the mouthpiece 54, thereby performing a classic Valsalva maneuver, albeit monitored and controlled by the programmer device 10 in the manner described above. As described above, the programmer device 10 will receive and analyze the finger plethysmogram signal obtained from the finger detector 46 during performance of the Valsalva maneuver. The resulting finger plethysmogram signal may be displayed on the programmer display/printer 42 and/or saved in programmer memory 38. The programmer processor 36 may analyze the finger plethysmogram signal to derive a quantitative pulmonary-capillary wedge pressure or related estimation from the signal. This value may be calculated from the finger plethysmogram signal in a conventional manner, as described above, displayed on the display/printer 42, and saved in memory 38. The clinician would then adjust one or more pacing parameters of the implanted device 12 using the programmer device 10 in a conventional manner. The patient 22 would then be sent home. After some period of time, needed to reach a steady state fluid balance, the patient 22 would return to the clinic, and the procedure of obtaining and analyzing a finger plethysmogram signal during performance of a controlled Valsalva maneuver would be repeated. One or more pacing parameters of the implanted device 12 may again be adjusted after the procedure. After several (e.g., three) such trials, the best pacing parameter for the implanted device 12 may be selected by choosing the pacing parameters which resulted in the most normal finger plethysmogram signal obtained during performance of the controlled Valsalva maneuver, or the pacing parameters yielding the lowest estimated pulmonary-capillary wedge pressure value calculated therefrom. (Preferably, each trial using a given pacing parameter may be repeated several times (e.g., three times), to improve the accuracy of the result.) The optimal pacing parameters may then be programmed into the implanted device using the programmer 10 in a conventional manner.

A programmer device 10 in accordance with the present invention may also or alternatively be employed to optimize the pacing parameters of an implanted pacing device 12 based on the analysis of pulsus alternans which may be detected in the finger plethysmogram signal provided by a finger detector 46. Heart failure patients with advanced ventricular dysfunction often have pulsus alternans. This pathological manifestation of the disease consists of pressure pulses that alternate in amplitude: strong, weak, strong, weak. In severe cases, the pulsus alternans can be palpated. The exact mechanism resulting in pulsus alternans in heart failure patients is unknown. However, the main known factors include inotropic alternation at the cellular level ($Ca^{2+}$ cycles) and secondary mechanical filling and loading alternations. It is known that pacing in congestive heart failure patients modifies ventricular filling (mechanical correction) and corrects conduction defects. Pulsus alternans have been observed to disappear in congestive heart failure patients when intracardiac conduction defects are corrected. Thus, improvement in cardiac performance resulting from optimization of pacing parameters can be observed by the resulting reduction of pulsus alternans in congestive heart failure patients receiving such therapy.

Figure 4:
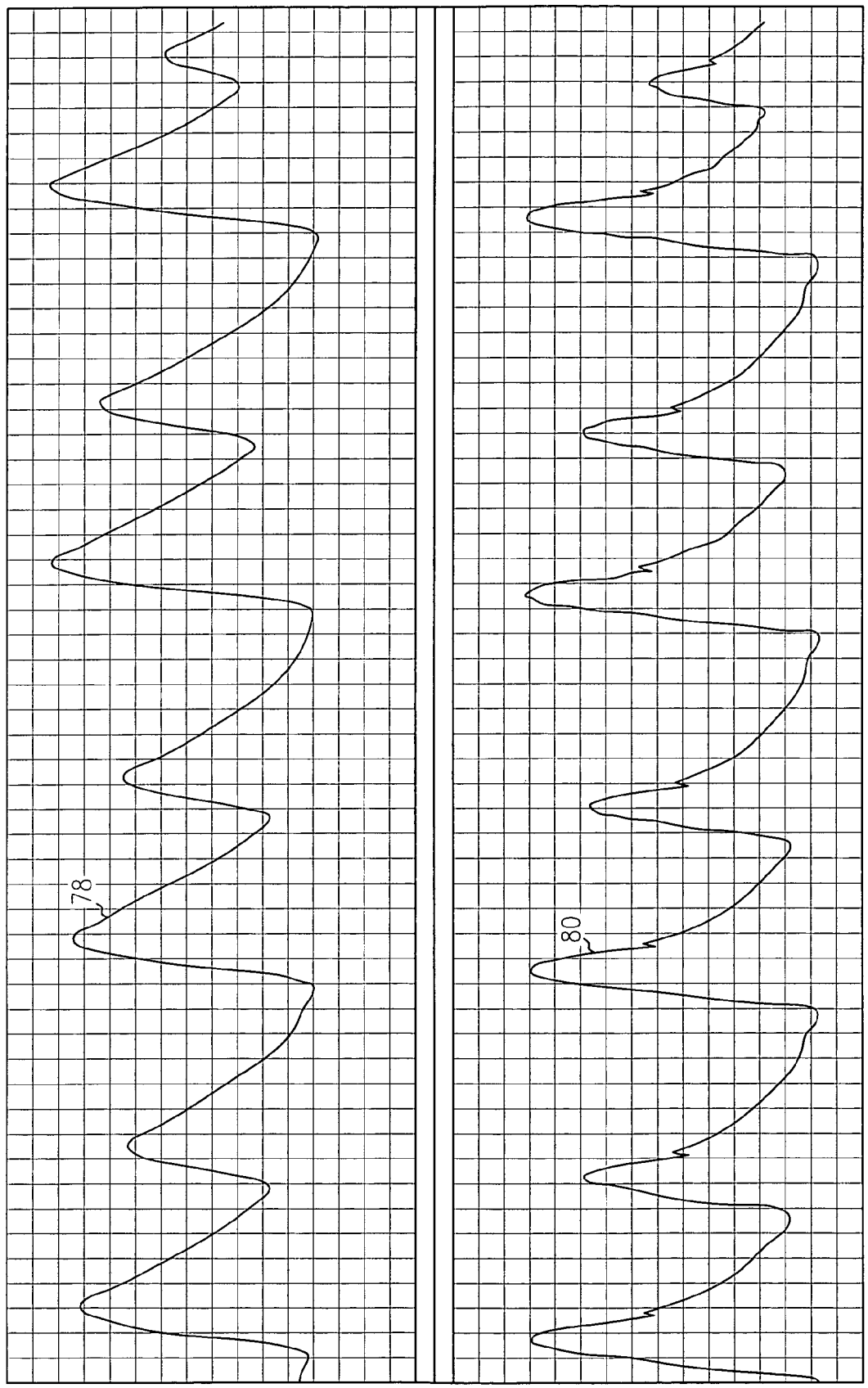
FIG. 4 is a waveform diagram showing pulsus alternans as detected using a finger plethysmogram sensor and an invasive catheter tip pressure transducer temporarily placed in the aorta of a patient.

As illustrated in FIG. 4, a finger plethysmogram signal 78 obtained from a finger detector 46 attached to a congestive heart failure patient reveals pulsus alternans as pulses of alternating amplitudes. Note that the finger plethysmogram signal 78 reflects the pulsus alternans which are apparent in a signal 80 obtained directly using, e.g., an implanted aortic pressure sensor. Thus, FIG. 4 illustrates that pulsus alternans can be detected accurately and, therefore, variations/reductions in pulsus alternans observed, using a finger detector 46 to obtain a finger plethysmogram signal.

Figure 5:
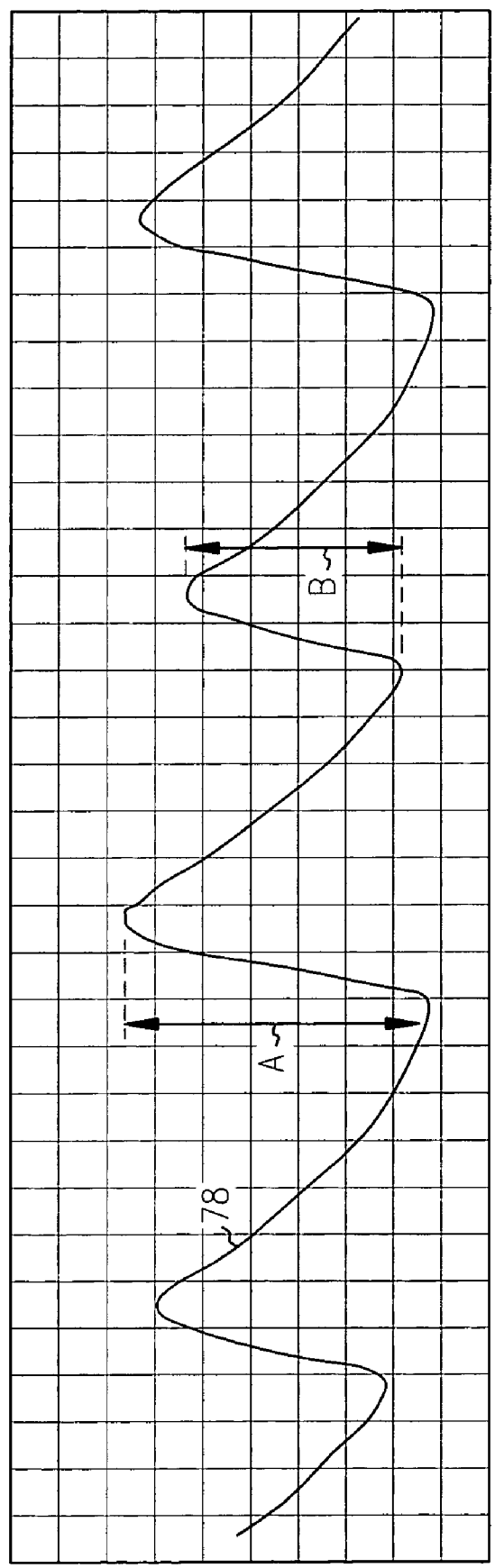
FIG. 5 is a waveform diagram illustrating a method of measuring a degree of pulsus alternans from a finger plethysmogram signal.

In accordance with the present invention, the programmer device 10 may be employed to analyze the finger plethysmogram signal obtained by a finger detector 46 to monitor the degree of pulsus alternans in heart failure patients, and to adjust the pacing parameters of an implanted pacing device 12 to minimize pulsus alternans thus detected. By measuring the pattern of alternans and the amplitude ratios in the plethysmogram signal, hemodynamic impairment amelioration can be monitored. Thus, for example, a clinician may observe the finger plethysmogram signal provided by the finger detector 46, as processed by the programmer processor 36 for display on programmer display/printer 42, resulting from the application of various different pacing parameters by the implanted pacing device 12. Those pacing parameters which result in a displayed finger plethysmogram signal showing the minimum degree of pulsus alternans may then be selected as the optimal pacing parameters to be used to program the implanted pacing device 12. More quantitatively, the programmer device processor 36 may be programmed to calculate a numerical value relating to the degree of pulsus alternans detected in a finger plethysmogram signal during application of particular pacing parameters by an implanted pacing device 12. For example, as illustrated in FIG. 5, the programmer processor 36 may calculate a degree of pulsus alternans as the amplitude ratio of the peak-to-peak amplitude a of the larger amplitude pulses detected in the finger plethysmogram signal to the peak-to-peak amplitude b of the smaller amplitude pulses detected in the finger plethysmogram signal. An average of such a ratio may be calculated for several series of beats detected during application of pacing using particular selected pacing parameters provided by the implanted device 12. The pacing parameters which result in the lowest average pulse amplitude ratio thus calculated may be selected as the optimum pacing parameters to be employed in the implanted pacing device 12. Of course, the programmer device processor 36 may also be programmed to derive a quantitative measurement of pulsus alternans in the finger plethysmogram signal 78 in any other manner.

Figure 6:
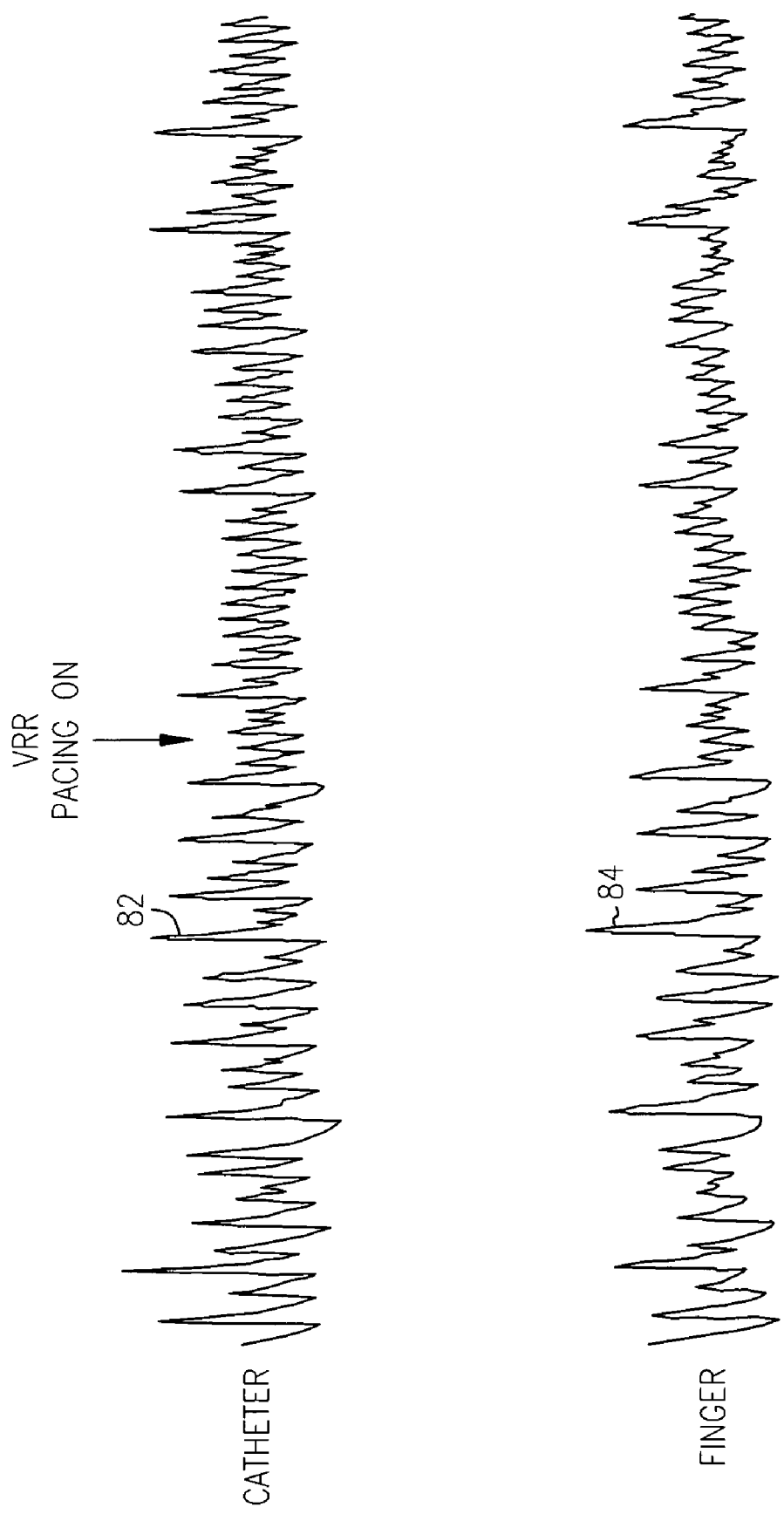
FIG. 6 is a waveform diagram illustrating relative changes in pulse pressure of an atrial fibrillation patient and the effect of pacing on the pressure signal obtained from an invasive catheter tip pressure transducer placed temporarily in the aorta of a patient and from a finger plethysmogram sensor.

A programmer device 10 in accordance with the present invention may also, or alternatively, be employed for optimizing the pacing parameters of an implanted pacing device 12 to obtain the best hemodynamic performance in an atrial fibrillation patient. Atrial fibrillation may result in irregular ventricular rhythm and pulse pressure. Pacing of the ventricles is employed to regulate the rhythm and pressure in the ventricles. As illustrated in FIG. 6, a pulse pressure signal 82 obtained from a pressure sensor implanted in the aorta of a patient experiencing atrial fibrillation shows irregular beat-to-beat pulse pressure. A corresponding finger plethysmogram signal 84 obtained from a finger detector 46 also reflects relative changes in pulse pressure. Note that the finger plethysmogram signal 84 tracks the pressure changes in the signal 82 obtained via direct measurement in the aorta of an atrial fibrillation patient. Thus, the finger plethysmogram signal 84 may be employed by a programmer device 10 in accordance with the present invention to optimize the pacing device 12 pacing parameters by adjusting the pacing device pacing parameters such that the pressure, as reflected in the finger plethysmogram signal, is regularized, and the peak amplitudes are more uniform.

For example, the programmer device 10 may command the implanted pacing device 12 to execute various known rate and pressurization regularization algorithms which are used to regulate ventricular activity of a patient experiencing atrial fibrillation. A finger plethysmogram, as obtained from the finger detector 46, is received by the programmer processor 36, and displayed on the display/printer 42 and/or saved in memory 38 as the implanted device 12 provides pacing using various different pacing parameters. After this procedure is complete, the programmer device 10 may print out and/or display a report of the pacing parameters that yield the best hemodynamic response based on the finger plethysmogram signal, e.g., the pacing parameters yielding the finger plethysmogram signal showing the most regularized and uniform peak amplitudes. For example, the pacing parameters resulting in the lowest average peak-to-peak amplitude variation in the finger plethysmogram signal may be selected as the optimum pacing parameters for an atrial fibrillation patient. Ventricular rate information could also be combined with the pressure uniformity data for selecting the pacing parameters. Thus, the present invention may be employed to optimize noninvasively pacing parameters of an implanted pacing device 12 providing therapy in an atrial fibrillation patient.

As discussed above, in accordance with the present invention, a finger plethysmogram signal is employed as a noninvasive measure of cardiac performance. This measure may be employed to monitor the progression of heart failure disease, to more accurately determine the optimum intervention to be employed in the overall management of the patient. Where pacing therapy is to be employed, the finger plethysmogram signal is employed by a programmer device 10 in accordance with the present invention to obtain optimum pacing parameters for an implanted pacing device 12. Various manual and/or automatic methods may be employed using the finger plethysmogram signal to obtain such optimum pacing parameters.

For example, as illustrated in FIG. 6, a finger plethysmogram signal 82 obtained from a finger detector 46 reflects changes in cardiac pulse pressure, e.g., as detected directly from a signal 84 provided by a pressure sensor positioned in a patient's aorta. As illustrated in FIG. 6, the finger plethysmogram signal tracks pressure changes as pacing is introduced, e.g., to a congestive heart failure patient. The finger plethysmogram signal 86 may thus be monitored during a pacing interval during which pacing is provided by the implanted pacing device 12 with pacing parameters set at given values. A selected pacing parameter may be incrementally changed, and monitoring of the finger plethysmogram signal repeated at each pacing interval corresponding to an increment of the selected pacing parameter. Between such pacing periods, the heart may be allowed to beat at a natural sinus rhythm, in order to establish a baseline for comparison. The programmer device processor 36 may be programmed, as described above, to analyze the finger plethysmogram signals obtained during such pacing intervals and to determine automatically therefrom the pacing parameters which result in the best hemodynamic performance (e.g., as discussed above, the finger plethysmogram signal resulting in reduced pulsus alternans, regularized pulse amplitude, etc.)

An exemplary method in accordance with the present invention for pacing the heart using various pacing parameters and monitoring a finger plethysmogram signal during such pacing to determine optimal pacing parameters will now be described in detail with reference to FIGS. 7 and 8. The method to be described is particularly useful for determining accurately the effect of pacing determined from a finger plethysmogram signal provided by a photoplethysmogram signal detector, which can be susceptible to noncardiogenic interference. This method may also be used with other types of non-invasive plethysmogram detectors to reject various other artifacts which may affect accurate determination of the cardiac effect of pacing as determined from the plethysmogram signal.

Figure 7:
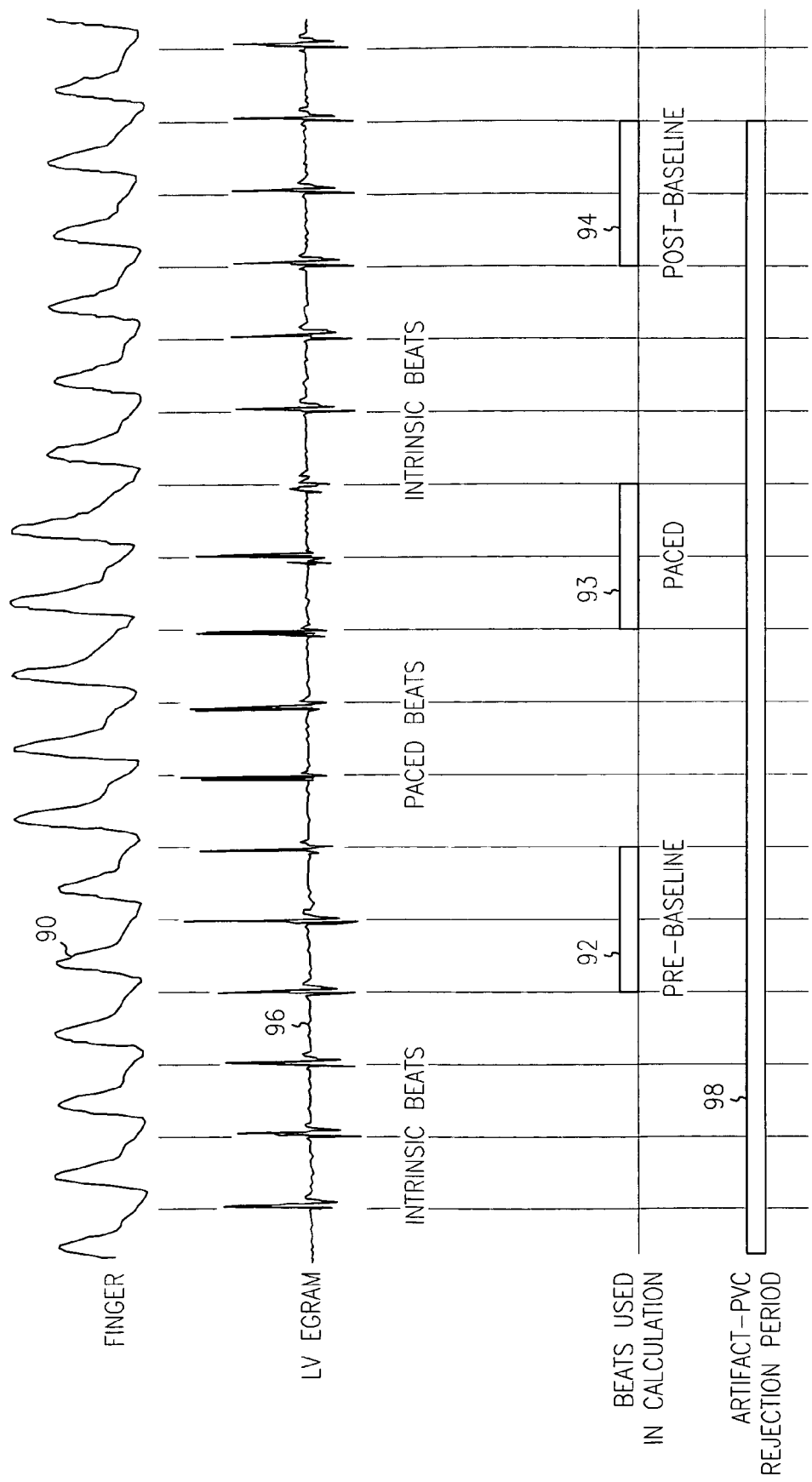
FIG. 7 is a waveform and timing diagram illustrating a method in accordance with the present invention for pacing the heart using various pacing parameters and monitoring a finger plethysmogram signal during such pacing to determine optimum pacing parameters in a manner which rejects noncardiogenic changes in the finger plethysmogram signal and other artifacts which may affect the accuracy of the determination.
Figure 8:
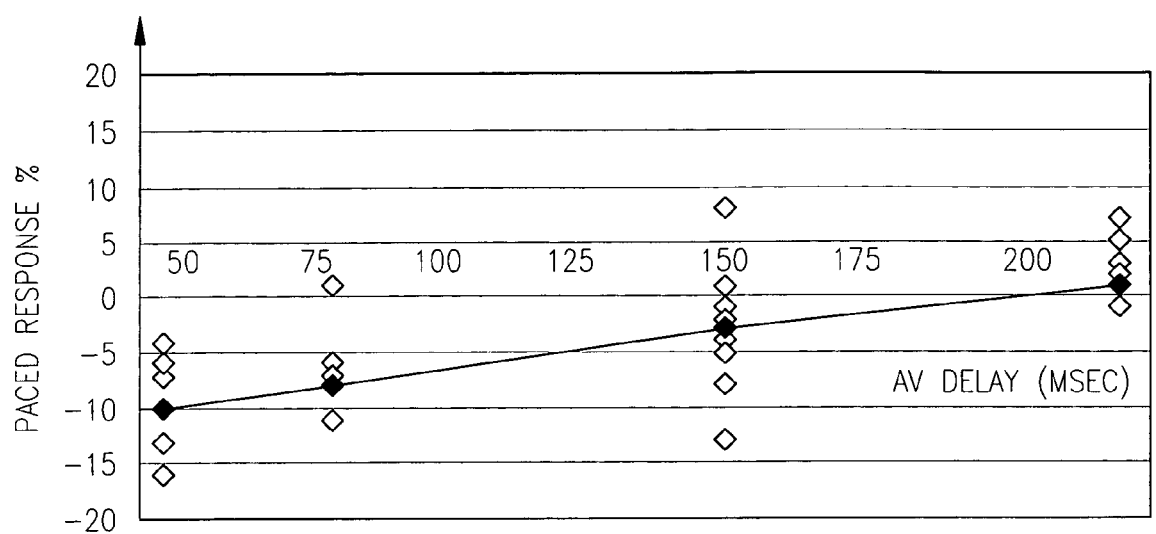
FIG. 8 is an exemplary graph derived from a series of paced responses as detected in finger plethysmogram signals obtained during pacing sequences using a series of AV delays to determine an optimum AV delay value.

As shown in FIG. 7, three groups of beats detected from the finger photoplethysmogram signal 90 are used in the calculation. Two beats are used from each of the groups of pre-baseline beats 92, obtained just before pacing commences, paced beats 93, obtained during pacing, and post-baseline beats 94, obtained after pacing has terminated. A pulse amplitude is computed for each of the three groups 92, 93, 94, as peak-to-peak amplitudes of the photoplethysmogram signal 90, with each group's figure being the average of its two beats. By obtaining the pre-baseline 92 and post-baseline 94 amplitudes, correction for noncardiogenic changes in finger pulse amplitudes detected in the photoplethysmogram signal 90 can be obtained. For example, if, after a deep breath, the autonomic reflex causes the finger pulse amplitude to decrease gradually, the pre-92 and post-94 baseline values will reflect this diminishing trend. Thus, the paced response 93, which is cardiogenic, can be corrected for the diminishing noncardiogenic component. The paced response may thus be calculated as: response %={(paced−pre-baseline)−(post-baseline−pre-baseline)/compensation factor}/pre-baseline. The compensation factor is determined by simple geometry or empirical calibration, and is a number in the range of 1 to 8. Simple conventional high pass filtering on the pulse amplitude signal may also preferably be employed to enhance the accuracy of the result.

The pacing sequence described, a series of paced beats separated by intrinsic baseline beats, is repeated a number of times (e.g., approximately 8 times) for each pacing parameter value (e.g., AV delay and pacing site combination) that is to be comparatively tested. Such repetitions further eliminate out the noncardiogenic components in the signal. The median of the several sequences is then taken as the resulting pacing response for the given pacing parameter value (AV delay and/or pacing site). A graph can then be drawn, as shown, for example, for AV delay, in FIG. 8. In the example shown, this allows for the determination of the best AV delay. (In this case, the best AV delay is the longest one (220 msec.).) This is the AV delay which results in the largest pulse amplitude response, i.e., the pacing parameter value which results in the largest pulse amplitude charge from baseline. In FIG. 8 the diamonds show the measurements performed at each pacing sequence. A line has been drawn connecting the medians of each AV delay group.

The method used for determining the effect of pacing from the finger plethysmogram signal should also reject the effects of other artifacts which might affect the accuracy of such a determination. For example, sudden movements of a patient's hand or arm will cause an artifact in the finger plethysmogram signal which should be detected and rejected from the calculation. Similarly, premature ventricular or atrial contractions (PVCs or PACs) will cause hemodynamic disturbances in the signal. These events may be detected by the programmer processor 36, from electrograms 96 detected by the implanted device 12 and telemetered to the programmer 10 in the manner as discussed above, and then rejected. This rejection may be done by discarding the affected pacing sequence, and repeating it. If baseline artifact checking is enabled 98, any beat that changes by more than a certain percentage in relation to the average of the preceding two beats is declared a baseline artifact. If the baseline artifact occurs during, e.g., the 5 to 8 beats preceding pacing, the pre-baseline is deemed corrupted, and more, e.g., 8 more, intrinsic beats are added to allow the artifact to wash out before pacing. If the artifact occurs after pacing, then the post-baseline is deemed corrupted, and the whole pacing sequence is repeated. For artifact detection in the beats after pacing, the comparison is made in relation to the pre-baseline value, or to that of preceding beats of the post-baseline. If any paced beat changes by more than a certain percentage of the pre-baseline, a pacing artifact is declared. This causes the sequence to be discarded and repeated. Any single PVC or PAC detected during the time of artifact rejection 98 will cause a response similar to an artifact detection, i.e., the pacing sequence is discarded and repeated.

It should be understood that a programmer device 10 in accordance with the present invention may be employed to optimize any pacing parameter of an implanted pacing device which would have an effect on hemodynamic response. For example, as discussed above, a programmer device 10 in accordance with the present invention may be employed to optimize the AV delay. Other pacing parameters which may be optimized using a programmer device 10 in accordance with the present invention include interventricular delay (i.e., the time delay between the stimulation of one ventricle and the stimulation of the other ventricle), pacing site (e.g., left ventricle, right ventricle, bi-ventricular, etc.), pacing energy (e.g., pulse width, pulse amplitude, pulse shape), pacing mode, etc. In any case, the present invention provides a method and device for optimizing such pacing parameters using a noninvasively obtained signal which corresponds to hemodynamic performance, i.e., a finger plethysmogram signal.

The present invention thus provides in a single programmer device the capability both to program an implanted cardiac pacing device and to determine non-invasively optimal pacing parameters for the implanted device, particularly for congestive heart failure patients. This is achieved by providing a finger plethysmogram signal to the programmer device from which optimal pacing parameters may be determined. The ability of the programmer device to control and monitor the performance of the Valsalva maneuver by a patient allows the device specifically to optimize pacing parameters based on changes in the finger plethysmogram related to pulmonary-capillary wedge pressure. For other physiologic conditions detectable from the finger plethysmogram and used for pacing parameter optimization (e.g., pulsus alternans), the ability of the programmer to control/monitor the Valsalva maneuver is not required.

A programmer device in accordance with the present invention may be employed more generally to monitor a patient's condition as it relates to heart failure. For example, by non-invasively determining an estimation of pulmonary capillary wedge pressure from a finger plethysmogram signal, and observing the Valsalva response using a programmer device in accordance with the present invention, clinical personnel at a pacemaker follow-up clinic can objectively detect a deterioration of the patient's general condition as it relates to heart failure. Pulsus alternans can also be detected as a deteriorating symptom of the heart failure patient. In this way, for example, an operator of a programmer device in accordance with the present invention can warn the heart failure specialist that, for example, the patient's estimated pulmonary wedge pressure is higher than measured at the last visit. This would indicate that a more thorough medical exam is in order, as well as a possible revision of medication prescription.

It is understood that the present invention is not limited to the particular exemplary applications and embodiments illustrated and described herein, but embraces such modified forms thereof come within the scope of the following claims.

What is claimed is:

1. An external programmer for an implantable cardiac pacing device, the external programmer comprising:
   a transmitter to transmit programming instructions to the implantable cardiac pacing device to program pacing parameters of the implantable cardiac pacing device;
   a finger plethysmogram signal detector to provide a finger plethysmogram signal; and
   a programmer processor coupled to the transmitter and the finger detector, the programmer programmed to generate the programming instructions, to control the transmitter for transmitting the programming instructions, to process the finger plethysmogram signal to detect pulsus alternans in the finger plethysmogram signal, and to derive a quantitative value related to a degree of the detected pulsus alternans.

2. The external programmer device of claim 1, wherein the finger plethysmogram signal detector comprises a finger clip signal detector.

3. The external programmer device of claim 1, wherein the finger plethysmogram signal detector comprises a photoplethysmogram signal detector.

4. The external programmer device of claim 3, wherein the finger plethysmogram signal detector comprises a pulse oximeter sensor.

5. An external programmer for an implantable cardiac pacing device, the external programmer comprising:
   a transmitter to transmit programming instructions to the implantable cardiac pacing device to program pacing parameters of the implantable cardiac pacing device;
   a finger plethysmogram signal detector to provide a finger plethysmogram signal; and
   a programmer processor coupled to the transmitter and the finger detector, the programmer programmed to generate first programming instructions to control the implantable cardiac pacing device to pace for a plurality of series of paced beats using different selected pacing parameter values for different series of paced beats, to control the transmitter for transmitting the first programming instructions, and to analyze a selected characteristic of the finger plethysmogram signal for each series of paced beats of the plurality of paced beats,
   wherein the selected characteristic of the finger plethysmogram signal is selected from at least one of a pulse amplitude detected from the finger plethysmogram signal and a degree of pulsus alternans detected from the finger plethysmogram signal.

6. The external programmer of claim 5, wherein the programmer processor is programmed to determine an approximately optimal pacing parameter value based on the analysis of the selected characteristic of the finger plethysmogram signal for the each series of paced beats of the plurality of paced beats.

7. The external programmer of claim 6, wherein the selected pacing parameter values includes values of at least an AV delay.

8. The external programmer of claim 6, wherein the selected pacing parameter values includes values of at least a pacing site parameter.

9. The external programmer of claim 6, wherein the selected pacing parameter values includes values of at least a pacing mode parameter.

10. The external programmer of claim 6, wherein the programmer processor is programmed to generate programming instructions to be transmitted to the implantable cardiac pacing device to control the implantable cardiac pacing device to pace for a plurality of series of paced beats separated by non-pacing beats.

11. The external programmer of claim 10, wherein the programmer processor is programmed to analyze characteristics of the finger plethysmogram signal during the paced beats in each series of the plurality of paced beats and during non-paced beats before and after each series of paced beats.

12. A non-invasive method for optimizing pacing parameters of a cardiac device implanted in a patient, the method comprising:
   detecting a finger plethysmogram signal from the patient during pacing with a selected pacing parameter value;
   monitoring a Valsalva maneuver performed by the patient while detecting the finger plethysmogram signal;
   analyzing the finger plethysmogram signal to obtain a cardiac performance parameter indicative of cardiac performance;
   adjusting the selected pacing parameter value; and
   obtaining an improvement in the cardiac performance parameter by repeating the detecting the finger plethysmogram signal, the monitoring the Valsalva maneuver, the analyzing the finger plethysmogram signal, and the adjusting the selected pacing parameter value.

13. The method of claim 12, wherein repeating the detecting the finger plethysmogram signal, the monitoring the Valsalva maneuver, the analyzing the finger plethysmogram signal, and the adjusting the selected pacing parameter value comprises repeating the detecting the finger plethysmogram signal, the monitoring the Valsalva maneuver, the analyzing the finger plethysmogram signal, and the adjusting the selected pacing parameter value for a plurality of pacing series intervals separated by periods of non-paced rhythm, wherein adjusting the selected pacing parameter value includes adjusting the selected pacing parameter value to a different value for each different pacing series interval of the plurality of pacing series intervals.

14. The method of claim 13, further comprising attaching a photoplethysmogram signal detector to the finger of the patient.

15. The method of claim 13, further comprising attaching a pulse oximeter sensor to the finger of the patient.

16. The method of claim 12, wherein analyzing the finger plethysmogram signal to obtain the cardiac performance parameter indicative of cardiac performance comprises analyzing the finger plethysmogram signal during performance of the Valsalva maneuver by the patient to obtain a cardiac performance parameter related to a filling pressure.

17. The method of claim 16, wherein the filling pressure comprises pulmonary-capillary wedge pressure.

18. The method of claim 16, wherein the filling pressure comprises left ventricular diastolic pressure.

19. A non-invasive method for optimizing pacing parameters of a cardiac device implanted in a patient, the method comprising:
   detecting a finger plethysmogram signal from the patient during pacing with a selected pacing parameter value;
   analyzing the finger plethysmogram signal to monitor a degree of pulsus alternans;
   adjusting the selected pacing parameter value; and reducing the degree of pulsus alternans by repeating the detecting the finger plethysmogram signal, the analyzing the finger plethysmogram signal, and the adjusting the selected pacing parameter value.

20. The method of claim 19, wherein analyzing the finger plethysmogram signal to monitor the degree of pulsus alternans comprises determining an amplitude ratio of pulses detected in the finger plethysmogram signal.

21. The method of claim 19, wherein reducing the degree of pulsus alternans comprises minimizing the degree of pulsus alternans.

22. The method of claim 21, wherein adjusting the selected pacing parameter value includes adjusting a value of one of an AV delay, a pacing site parameter, and a pacing mode parameter.

23. A non-invasive method for optimizing pacing parameters of a cardiac device implanted in a patient, the method comprising:
   detecting a finger plethysmogram signal from the patient during pacing with a selected pacing parameter value;
   analyzing the finger plethysmogram signal to monitor a finger plethysmogram pulse amplitude in response to the pacing;
   adjusting the selected pacing parameter value; and
   increasing the finger plethysmogram pulse amplitude in response to the pacing by repeating the detecting the finger plethysmogram signal, the analyzing the finger plethysmogram signal, and the adjusting the selected pacing parameter value.

24. The method of claim 23, wherein increasing the finger plethysmogram pulse amplitude in response to the pacing comprises maximizing the finger plethysmogram pulse amplitude in response to pacing.

25. The method of claim 24, wherein adjusting the selected pacing parameter value includes adjusting a value of one of an AV delay, a pacing site parameter, and a pacing mode parameter.

26. A non-invasive method for optimizing pacing parameters of a cardiac device implanted in a patient, the method comprising:
   detecting a finger plethysmogram signal from the patient during pacing with a selected pacing parameter value;
   analyzing the finger plethysmogram signal to monitor pulse pressure;
   adjusting the selected pacing parameter value; and
   regularizing the pulse pressure by repeating the detecting the finger plethysmogram signal, the analyzing the finger plethysmogram signal, and the adjusting the selected pacing parameter value.

27. The method of claim 26, wherein analyzing the finger plethysmogram signal to monitor pulse pressure comprises analyzing the finger plethysmogram signal to detect peak amplitudes of pulses in the finger plethysmogram signal, and regularizing the pulse pressure comprises making the peak amplitudes of pulses in the finger plethysmogram signal more uniform.

28. The method of claim 27, wherein adjusting the selected pacing parameter value includes adjusting a value of one of an AV delay, a pacing site parameter, and a pacing mode parameter.

29. A non-invasive method for optimizing pacing parameters of a cardiac device, the method comprising:
   delivering a pacing sequence including a plurality of series of paced beats, each of the series of paced beats preceded and followed by a series of non-paced beats and associated with one value of at least one pacing parameter, with a different value of the at least one pacing parameter used for each of the series of paced beats;
   detecting a finger plethysmogram signal during the delivery of the pacing sequence;
   analyzing the finger plethysmogram signal to monitor a parameter indicative of cardiac performance; and
   optimizing the at least one pacing parameter based on the analysis of the finger plethysmogram signal.

30. The method of claim 29, wherein analyzing the finger plethysmogram signal comprises analyzing the finger plethysmogram signal to monitor the parameter indicative of cardiac performance for each series of the plurality of series of paced beats, and wherein optimizing the at least one pacing parameter comprises determining the value of the at least one pacing parameter associated with the best cardiac performance as indicated by the finger plethysmogram signal.

31. The method of claim 30, wherein the parameter indicative of cardiac performance comprises a degree of pulsus alternans, and wherein optimizing the at least one pacing parameter comprises determining the value of the at least one pacing parameter associated with a minimum degree of pulsus alternans.

32. The method of claim 30, wherein the parameter indicative of cardiac performance comprises a pulse amplitude of the finger plethysmogram, and wherein optimizing the at least one pacing parameter comprises determining the value of the at least one pacing parameter associated with a maximum pulse amplitude of the finger plethysmogram.

33. The method of claim 30, wherein the parameter indicative of cardiac performance comprises peak amplitudes of the finger plethysmogram, and wherein optimizing the at least one pacing parameter comprises determining the value of the at least one pacing parameter associated with most uniform peak amplitudes of the finger plethysmogram.

34. The method of claim 30, wherein optimizing the at least one pacing parameter comprises optimizing an AV delay.

35. The method of claim 30, wherein optimizing the at least one pacing parameter comprises optimizing pacing sites.

* * * * *

UNITED STATES PATENT AND TRADEMARK OFFICE
CERTIFICATE OF CORRECTION

PATENT NO. : 7,366,569 B2
APPLICATION NO. : 10/941427
DATED : April 29, 2008
INVENTOR(S) : Belalcazar Page 1 of 1

It is certified that error appears in the above-identified patent and that said Letters Patent is hereby corrected as shown below:

In column 21, line 10, in Claim 21, delete "altermans" and insert -- alternans --, therefor.

Signed and Sealed this

Twenty-ninth Day of July, 2008

JON W. DUDAS
*Director of the United States Patent and Trademark Office*